US012648863B2

(12) United States Patent　　(10) Patent No.:　US 12,648,863 B2
Oglaza　　(45) Date of Patent:　Jun. 9, 2026

(54) SYSTEMS FOR DEPLOYING AN IMPLANT

(71) Applicant: Stryker Corporation, Portage, MI (US)

(72) Inventor: Jean-François Oglaza, Pins-Justaret (FR)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 19/102,511

(22) PCT Filed: Aug. 9, 2023

(86) PCT No.: PCT/US2023/029797

§ 371 (c)(1),
(2) Date: Feb. 10, 2025

(87) PCT Pub. No.: WO2024/035755

PCT Pub. Date: Feb. 15, 2024

(65) Prior Publication Data

US 2026/0053639 A1　　Feb. 26, 2026

Related U.S. Application Data

(60) Provisional application No. 63/396,743, filed on Aug. 10, 2022.

(51) Int. Cl.
A61F 2/46 (2006.01)
*A61B 17/00* (2006.01)

(52) U.S. Cl.
CPC ... A61F 2/4611 (2013.01); *A61B 2017/00477* (2013.01)

(58) Field of Classification Search
CPC .. A61B 17/8872; A61F 2/4603; A61F 2/4611; A61F 2002/4615
See application file for complete search history.

(56) References Cited

U.S. PATENT DOCUMENTS 7,824,427 B2 * 11/2010 Perez-Cruet ......... A61F 2/4611
　　　　　　　　　　　　　　623/17.11
8,986,386 B2 3/2015 Oglaza et al.
(Continued)

FOREIGN PATENT DOCUMENTS

EP　　　　2724680 A1　4/2014
WO　　2022162418 A1　8/2022

OTHER PUBLICATIONS

International Search Report for Application No. PCT/US2023/029797 dated Dec. 11, 2023, 2 pages.

*Primary Examiner* — Larry E Waggle, Jr.
(74) *Attorney, Agent, or Firm* — Howard & Howard Attorneys PLLC

(57) ABSTRACT

Systems and methods for deploying an implant. An introducer device includes an actuator, a shaft, a tensioning element coupled to the actuator, and an anchor coupled to the tensioning element. The implant includes a proximal neck configured to be removably disposed within a distal portion of the shaft. The proximal neck defines a notch sized to receive the anchor such that the distal portion of the shaft covers the anchor and prevents separation of the anchor from the notch with the tensioning element in a tensioned state. The actuator is configured to be actuated to release tension on the tensioning element so as to permit removal of the proximal neck from the distal portion of the shaft and separation of the anchor from the notch to decouple the implant from the introducer device. The anchor and the proximal notch may include complementary sloped surfaces to facilitate the separation.

20 Claims, 10 Drawing Sheets

(56)         References Cited

U.S. PATENT DOCUMENTS

| 9,414,933 | B2 | | 8/2016 | Banouskou |
| 11,219,536 | B2 | * | 1/2022 | Arramon ............... A61F 2/4637 |
| 2008/0281364 | A1 | | 11/2008 | Chirico et al. |

* cited by examiner

SYSTEMS FOR DEPLOYING AN IMPLANT

TECHNICAL FIELD

This application is a national entry of International Patent Application No. PCT/US2023/029797, filed on Aug. 9, 2023, which claims priority to and all the benefits of U.S. Provisional Patent Application No. 63/396,743, filed on Aug. 10, 2022, the entire contents of each being hereby incorporated by reference.

TECHNICAL FIELD

The present disclosure is directed to systems and methods for deploying an implant. More particularly, but not exclusively, the present disclosure is directed to systems and methods for stabilizing a vertebral body by providing improved releasable engagement between the implant and an introducer device.

BACKGROUND

A common source of back pain is a vertebral compression fracture in which a weakened or injured vertebral body loses height or collapses. The weakening of the vertebral body may be due to acute injury or, more often, degenerative changes such as osteoporosis. The compression fractures often appear on lateral radiographs as wedge deformities with greater loss of height anteriorly.

A manner of restoring height of the vertebral body includes deploying an implant within the vertebral body with an introducer device. The introducer device may be actuated to expand the implant to elevate or restore the height of the vertebral body. The implant remains within the vertebral body to enhance and maintain structural integrity of the vertebral body at the elevated or restored height. During the actuation of the introducer device and the expansion of the implant, the implant may twist or become misaligned if not sufficiently rotationally secured to the introducer device. This could lead to improper placement and/or expansion of the implant. Moreover, often with the implant still attached to the introducer device, a bone cement may be delivered in and/or around the implant to interdigitate with the surrounding cancellous bone so as to cure and stabilize the implant within the vertebral body. Again, if the implant and introducer device are not sufficiently secured, the bone cement may leak into undesirable areas of the vertebral body and/or forces from the bone cement may prematurely detach the implant from the introducer device. Such detachment could cause the implant to shift or move such that the implant is improperly positioned.

Accordingly, there is a need for an implant that remains sufficiently secured to the introducer device during deployment to then be separated in situ in an intuitive, ergonomic, and repeatable manner.

SUMMARY

The system and methods disclosed herein overcome the aforementioned challenges. According to certain implementations, a system for stabilizing a vertebral body is provided. The system includes an introducer device and an implant. The introducer device includes a handle, an actuator, a shaft extending from the handle, a tensioning element coupled to the actuator and extending along the shaft, and an anchor coupled to the tensioning element. The implant includes a proximal neck configured to be removably disposed within a distal portion of the shaft. The proximal neck defines a notch sized to receive the anchor such that the distal portion of the shaft covers the anchor and prevents separation of the anchor from the notch with the tensioning element in a tensioned state. The actuator is configured to be actuated to release tension on the tensioning element so as to permit removal of the proximal neck from the distal portion of the shaft and separation of the anchor from the notch and decouple the implant from the introducer device.

In certain implementations, the system includes an access cannula, an introducer device, and an implant. The introducer device includes a handle, an actuator, a shaft extending from the handle and deployable through the access cannula, a tensioning element coupled to the actuator and extending along the shaft, and an anchor coupled to the tensioning element. The anchor includes a first sloped surface. The implant includes a proximal neck configured to be removably disposed within a distal portion of the shaft. The proximal neck includes a second sloped surface and defines a notch sized to receive the anchor such that the first sloped surface and the second sloped surface abut one another with the tensioning element in a tensioned state. The actuator is configured to be actuated to release tension on the tensioning element so as to permit the first sloped surface and the second sloped surface to slidably move past one another to facilitate ejection of the anchor from the notch and decouple the implant from the introducer device.

In certain implementations, the system includes an introducer device and an implant. The introducer device includes a handle, an actuator, a shaft extending from the handle and comprising a distal portion defining a bore, a tensioning element coupled to the actuator and extending along the shaft, and an anchor coupled to the tensioning element. The implant includes a proximal neck removably extending within the distal portion of the shaft. The proximal neck defines a notch engaging the anchor with the tensioning element in a tensioned state. The actuator is configured to be actuated to release tension on the tensioning element in which the tensioning element is slidable within the handle by a distance greater than a length of the distal portion within which the proximal neck removably extends so as to facilitate decoupling the implant from the introducer device.

In certain implementations, the system includes an introducer device and an implant. The introducer device includes a handle, an actuator, a shaft extending from the handle, a tensioning element coupled to the actuator and extending along the shaft, and an anchor coupled to the tensioning element. The implant includes a proximal neck configured to be removably disposed within a distal portion of the shaft. The proximal neck defines a notch sized to receive the anchor with the tensioning element in a tensioned state. The proximal neck includes an anti-rotation feature positioned radially offset from the notch and configured to engage a complementary anti-rotation feature of the distal portion of the shaft.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
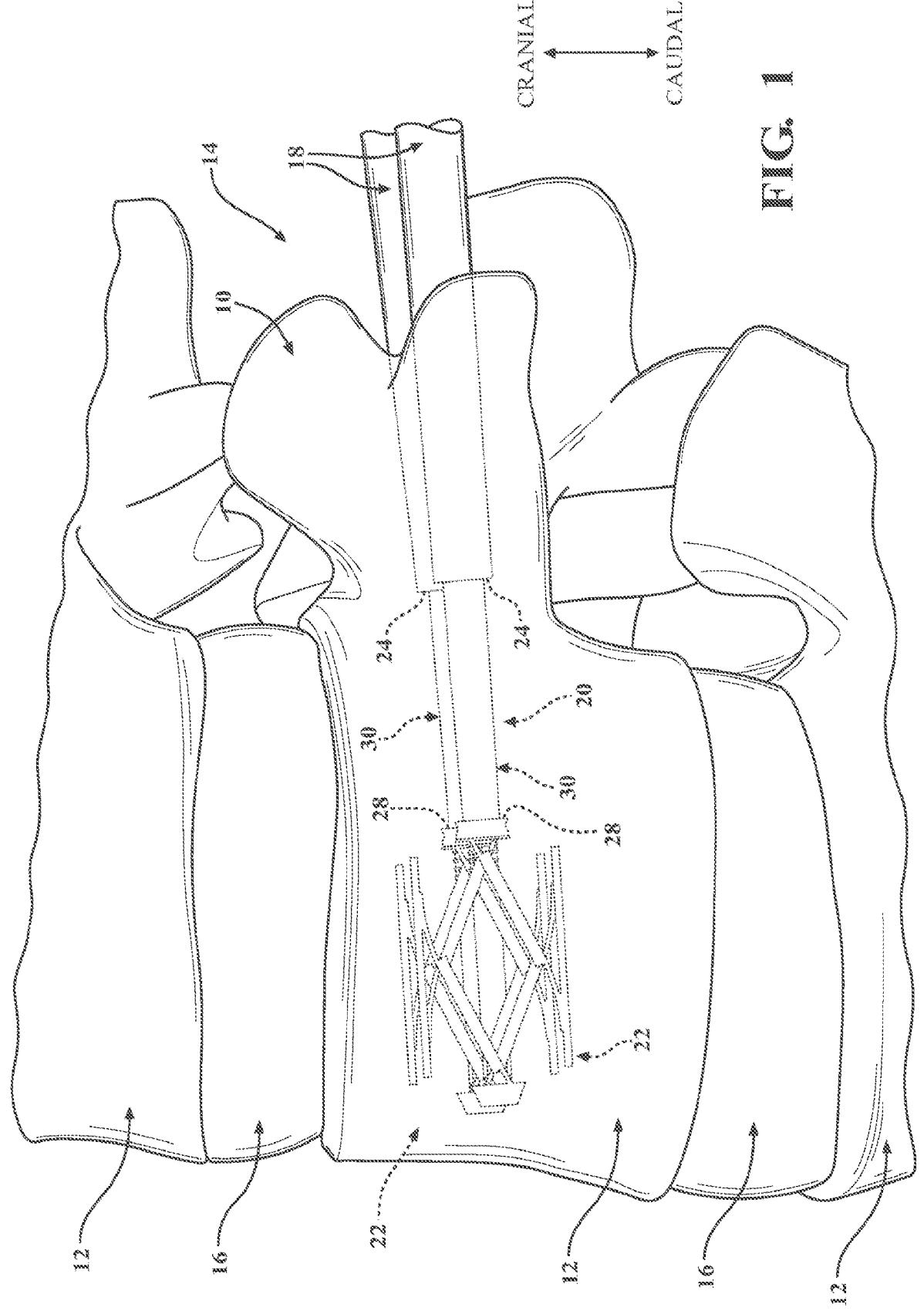
FIG. 1 is an illustration of a portion of a spine showing three vertebrae separated by two intervertebral discs with implants deployed within a vertebral body.

Referring to FIG. 1, an illustration of vertebrae 14 separated by intervertebral discs 16 is provided. Each of the vertebrae 14 includes a vertebral body 12 defining an interior region having cancellous bone. Anatomical directions may also be referenced herein in accordance with standard medical convention; i.e., cranial towards the head of patient or upwardly, caudal towards the feet of the patient or downwardly, distal towards an end of the device inserted first into the patient (or away from the practitioner), and proximal towards the practitioner.

A system 10 for stabilizing the vertebral body 12 may include an access cannula 18, an introducer device 20, and an implant 22. FIG. 1 shows the implant 22 in a deployed configuration that augments the vertebral body 12 to an elevated or restored height in a manner to be described. With the vertebral body 12 at the restored height, endplates of the vertebral body 12 are spaced farther apart from one another than in the unrestored height, which may reduce or eliminate pain and other sequelae associated with compression fracture.

The access cannula 18 includes a distal end 24 configured to be directed through a pedicle to access the interior region of the vertebral body 12. A trocar (not shown) may include a solid shaft sized to be removably disposed within the access cannula 18. The trocar may include a length slightly greater than a length of the cannula such that a sharp tip of the trocar pierces the cortical bone of the pedicle, and the trocar prevents coring of tissue within a lumen of the access cannula 18. Once the distal end 24 of the access cannula 18 is positioned within the vertebral body 12, the trocar is removed. The access cannula 18 provides a working channel to within the interior region of the vertebral body 12 along an axis. The inner diameter of the access cannula 18 is at least sufficient to receive the introducer device 20 and the implant 22 to be deployed. A cavity creator (not shown) may be directed through the working channel to within the vertebral body 12. The cavity creator may be operated (e.g., rotated) to create a generally cylindrical cavity within the cancellous bone with the cavity being approximate to the size of the implant 22.

Figure 2:
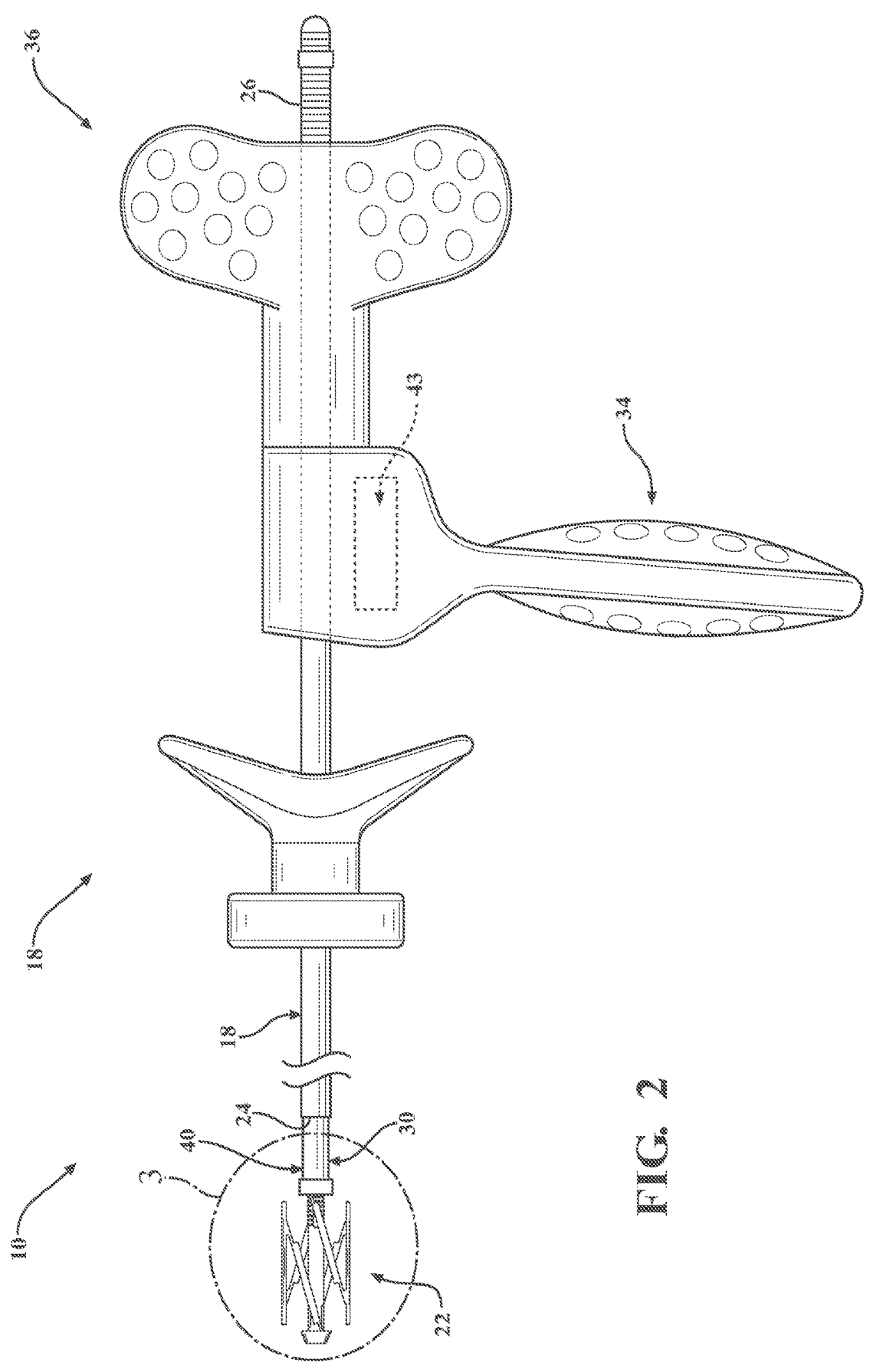
FIG. 2 is an elevation view of a system including the implant, an access cannula, and an introducer device actuated to deploy the implant.
Figure 3:
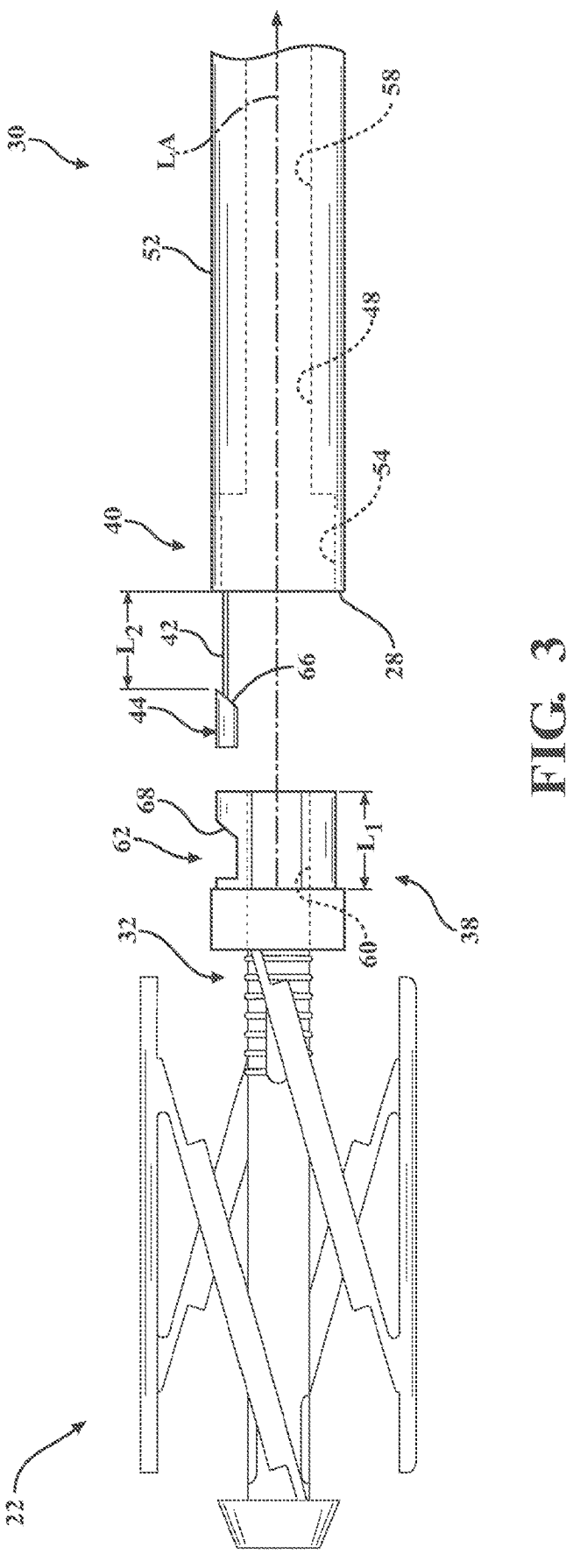
FIG. 3 is an enlarged exploded view taken at reference 3 in FIG. 2, shown with the introducer device spaced from the implant.
Figure 4:
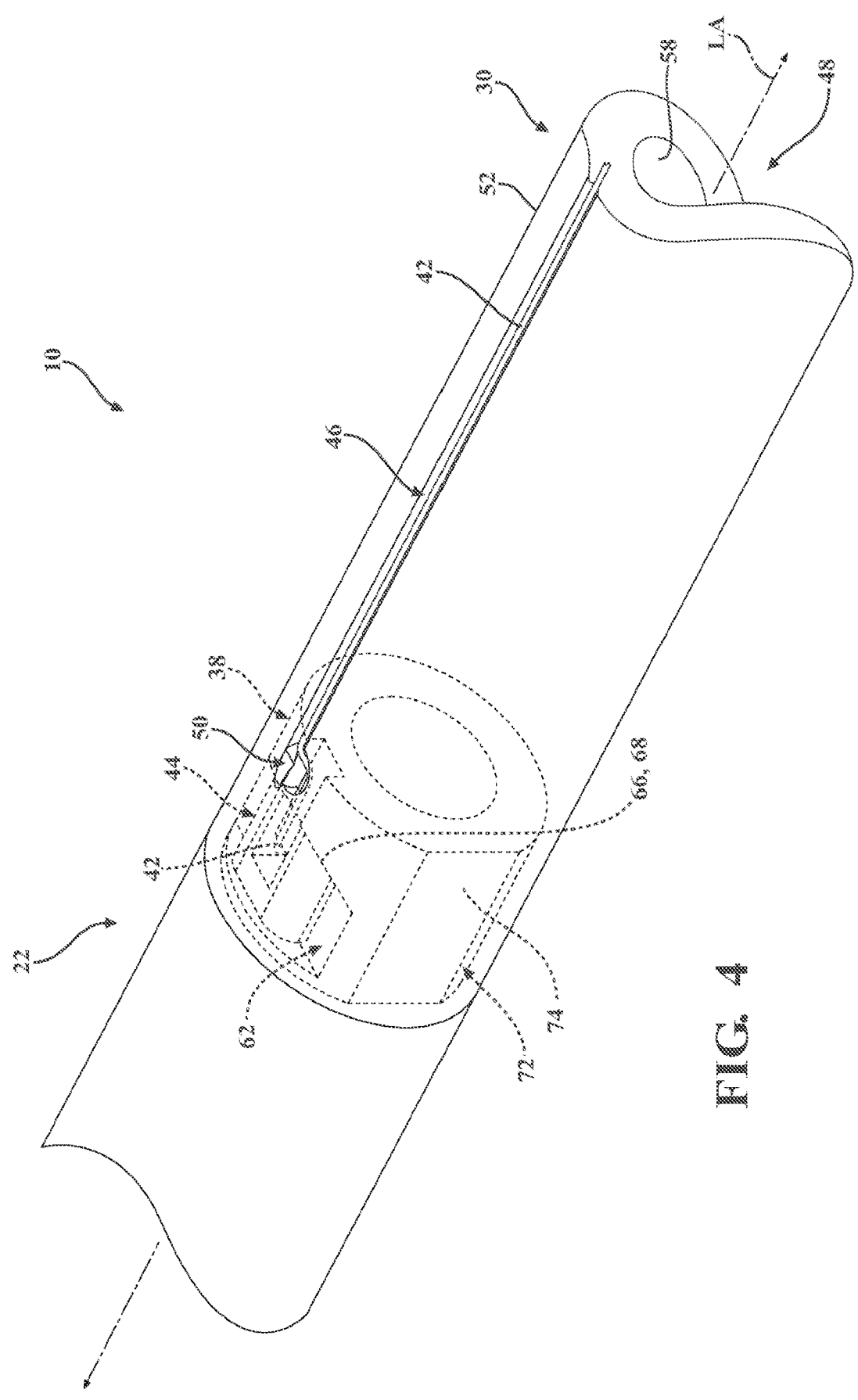
FIG. 4 is a partial perspective view of the system in which a proximal neck of the implant is disposed within a distal portion of the introducer device. A tensioning element of the introducer device may be in a tensioned state.

The introducer device 20 includes a proximal end, a distal end 28, and a shaft 30 extending distally from a handle 34. The shaft 30 has a distal portion 40 extending to the distal end 28 of the introducer device 20. FIGS. 2-4 generally reflect the distal portion 40 of the shaft 30 being coupled to the implant 22, and more particularly to a proximal neck 38 of the implant 22. The introducer device 20 may include the handle 34 and an implant actuator 36 (see FIGS. 2 and 10A-11B) configured to receive an input of the user to deploy the implant 22. The implant actuator 36 may be operably coupled to a retaining element 32 of the implant 22 and configured to proximally draw a distal end of the implant 22. Upper and lower plates of the implant 22 are moved away from one another in the craniocaudal direction to restore the height of the vertebral body 12, in effect moving the implant 22 to the deployed configuration shown in FIG. 1. Further operation of the introducer device 20 and its interfacing with the retaining element 32 of the implant 22 is described in commonly owned U.S. Pat. No. 8,986, 386, issued Mar. 24, 2015, and U.S. Pat. No. 9,414,933, issued Aug. 16, 2016, the entire contents of each being hereby incorporated by reference. In procedures utilizing a bipedicular approach, the workflow is repeated through the contralateral pedicle, which is reflected in FIG. 1 showing two systems 10 deploying two implants 22 within the same vertebral body 12. Alternatively, a unipedicular approach may include utilizing a singular system 10 with a singular implant 22.

With the implant 22 deployed, a rod 26 of the introducer device 20 may be decoupled from the implant 22 and removed from the shaft 30 of the introducer device 20. The shaft 30 remains coupled to the implant 22. Bone cement may be directed through the shaft 30 of the introducer device 20 in communication with apertures of the retaining element 32 to exit into the vertebral body 12 surrounding the implant 22. Therefore, it is necessary for the implant 22 to be sufficiently secured to the shaft 30 of the introducer device 20 during the impregnation of the vertebral body 12 with the bone cement, which may be associated with appreciable viscous forces. One a desired quantity of the bone cement has been placed, a limited period of time exists for the introducer device 20 to be decoupled from the implant 22 and removed from the access cannula 18 prior to the hardening of the bone cement.

The system 10 of the present disclosure addresses the aforementioned considerations by securely coupling to the implant 22 to the introducer device 20 such that any unintentional shifting or decoupling between the implant 22 and the introducer device 20 is prevented. Further, the introducer device 20 may be selectively separated from the implant 22 in an intuitive, ergonomic, and repeatable manner with little or no disruption to the position of the implant 22 within the vertebral body 12. Referring now to FIG. 3, the implant 22 includes the proximal neck 38, which may extend from or be formed as a proximal end portion of the implant 22. The implant 22 may be coupled to the introducer device 20 by positioning the proximal neck 38 of the implant 22 within an opening or counterbore 54 defined by the distal portion 40 of the shaft 30. The distal portion 40 of the shaft 30 overlaps at least a portion of the proximal neck 38 of the implant 22.

The introducer device 20 includes a tensioning element 42 coupled to an actuator 43 (see FIGS. 10A-11B), and an anchor 44 coupled to the tensioning element 42. As will be discussed in greater detail below, the anchor 44 is configured to engage the proximal neck 38 of the implant 22. With the anchor 44 of the introducer device 20 engaging the proximal neck 38 of the implant 22, the distal portion 40 of the shaft 30 covers at least a portion of the proximal neck 38 engaged by the anchor 44. In this way, the distal portion 40 prevents separation or disengagement of the anchor 44 from the proximal neck 38. The proximal neck 38 may define a notch 62 sized to receive the anchor 44. The anchor 44 may be sized and contoured to adjacent portions of the proximal neck 38 to define a generally semicircular contour. Therefore, with the anchor 44 disposed within the notch 62, an inner diameter of the distal portion 40 of the shaft 30 snugly covers the anchor 44 received within the notch 62 (see FIG. 4). The distal portion 40 of the shaft 30 encases the anchor 44 and prevents the anchor 44 from ejecting or separating from the notch 62 while the proximal neck 38 is maintained within the distal portion 40 of the shaft 30.

The tensioning element 42 cooperates with the aforementioned arrangement to facilitate coupling and decoupling of the implant 22 and the introducer device 20. The tensioning element 42 may be removably disposed within a slot 64 of the proximal neck 38 to provide the generally semicircular contour. In a tensioned state, the tensioning element 42 prevents separation of the implant 22 from the introducer device 20 by preventing the proximal neck 38 from being removed from the distal portion 40. In a released state in which there is little or no tension on the tensioning element 42, the tensioning element 42 facilitates decoupling of the implant 22 from the introducer device 20 by permitting the proximal neck 38 to be removed from the distal portion 40, after which the anchor 44 can eject or separate from the notch 62. Therefore, the tensioning element 42 and the anchor 44 are configured to prevent undesired separation of the implant 22 from the introducer device 20, and permit desired separation in an efficient manner to be described in greater detail. The tensioning element 42 may be a wire, band, braid, or the like and made of any suitable material. It will be appreciated that the tensioning element 42 may include any number of wires, bands, or the like, and may be flexible or rigid.

The shaft 30 may define a channel 46 extending longitudinally along the shaft 30, a shaft lumen 48, and an aperture 50 extending between an outer surface 52 of the shaft 30 and the shaft lumen 48 (see FIG. 4). The channel 46 may be defined in the outer surface 52 of the shaft 30. The tensioning element 42 is disposed within the channel 46 and passes through the aperture 50 to extend out of the shaft lumen 48 of the distal portion 40 of the shaft 30. Alternatively, the channel 46 may be defined along the shaft lumen 48 in which it may not be necessary for the tensioning element 42 to pass through the aperture 50. It is contemplated that the shaft 30 may define any number of channels extending in any direction. It is further contemplated that the shaft 30 and the proximal neck 38 may be generally tubular as shown or of any suitable shape to facilitate coupling of the introducer device 20 and the implant 22.

Referring again to FIG. 3, the proximal neck 38 of the implant 22 has a first length L1 corresponding generally to a length by which the proximal neck 38 extends into the distal portion 40 of the shaft 30. The length may be defined between the widened proximal end portion distal to the proximal neck 38 and a proximal end of the implant 22. The tensioning element 42 has a second length L2 to which the tensioning element 42 is configured to extend between the tensioned state and the released state. Stated differently, transitioning between the tensioned state and the released state is configured to permit the anchor 44 to move away from a distal end of the shaft 30 by at least the second length L2. The second length L2 of the tensioning element 42 is greater than the first length L1 of the proximal neck 38. In this way, in the released state, the second length L2 permits the anchor 44 to move away from a distal end of the shaft 30 by a distance sufficient to permit the proximal neck 38 to be removed from the distal portion 40, after which the implant 22 may be separated from the notch 62.

The notch 62 and anchor 44 are shaped so as to facilitate sturdy engagement between the introducer device 20 and the implant 22 in the tensioned state, yet further shaped to facilitate separation in the released state. In the illustrated implementation, the anchor 44 includes a first sloped surface 66, and the notch 62 includes a second sloped surface 68. The second sloped surface 68 of the notch 62 is configured to engage the first sloped surface 66 of the anchor 44. The arrangement places resistance on the movement of the anchor 44 with the encasement of the anchor 44 within the distal portion 40 of the shaft 30. The first sloped surface 66 and the second sloped surface 68 are complementarily oriented at angles so as to permit the anchor 44 to slidably eject from the notch 62 with proximal movement of the proximal neck 38 relative to the distal portion 40 of the shaft 30. More particularly, the first sloped surface 66 and the second sloped surface 68 slide along one another once the tensioning element 42, in the released state, has fully extended. Further proximal movement of the introducer device 20 causes the tensioning element 42 to pull on the anchor 44, after which it slidably ejects from the notch 62 to be removed with the access cannula 18 with the introducer device 20. It should be appreciated that the notch 62 and anchor 44 may assume any suitable complementary shapes, configurations, profiles, and the like.

Figure 5:
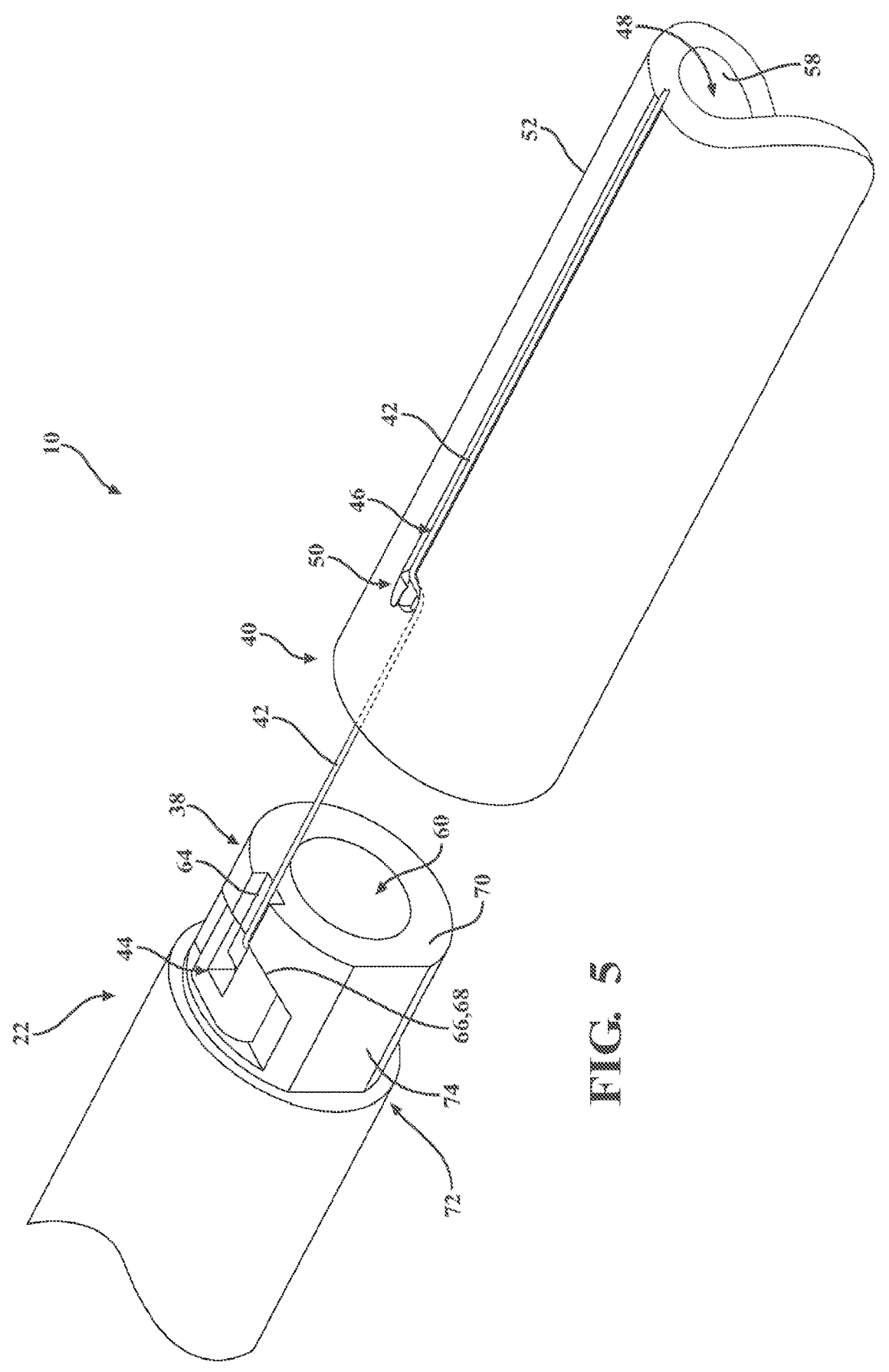
FIG. 5 is another partial perspective view of the system in which the proximal neck is separated from the distal portion and an anchor of the introducer device is within a notch defined by the proximal neck. The tensioning element may be in a released state.
Figure 6:
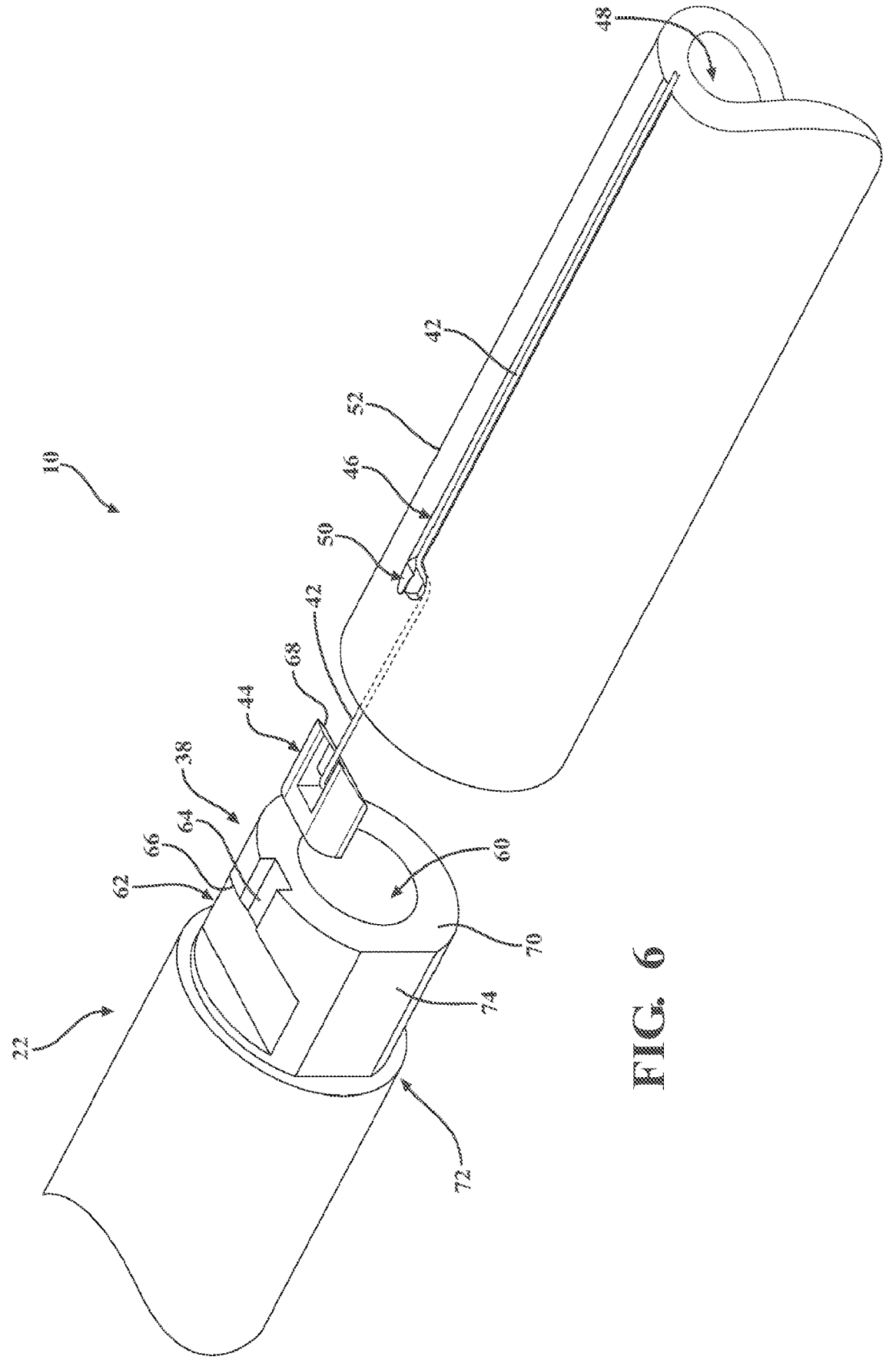
FIG. 6 is another partial perspective view of the system in which the anchor has ejected or separated from the notch to decouple the implant from the introducer device. The tensioning element is in the released state.

FIGS. 4-6 illustrate various stages of coupling and decoupling of the introducer device 20 and the implant 22. Starting with FIG. 4, the implant 22 is coupled to the introducer device 20. The proximal neck 38 is disposed within the distal portion 40. The anchor 44 is disposed within the notch 62. The first sloped surface 66 of the anchor 44 and the second sloped surface 68 of the proximal neck 38 abut one another. The distal portion 40 is covering the anchor 44 such that it is prevented from ejecting from the notch 62. The tensioning element 42 may be in the tensioned state (or in the released state prior to movement of the introducer device 20). In the tensioned state, the tensioning element 42 is tensioned and/or pulled proximally. In the tensioned state, the tensioning element 42 pulls the anchor 44 in the longitudinal direction such that the first sloped surface 66 of the anchor 44 and the second sloped surface 68 of the proximal neck 38 abut one another. The implant 22 and introducer device 20 are substantially immovable relative to one another while the tensioning element 42 is in the tensioned state. In this way, the implant 22 is prevented from separating from the introducer device 20, and the user may manipulate the introducer device 20 with corresponding movement of the implant 22.

The actuator 43 is actuated to move the tensioning element 42 from the tensioned state to the released state. The actuator 43 releases tension on the tensioning element 42 to permit movement of the tensioning element 42 relative to the handle 34, and relative to the shaft 30. FIG. 5 is indicative of the tensioning element 42 in the released state and the user moving the introduce device 20 away from the implant 22, such as to be removed from the access cannula 18. The anchor 44 may still be disposed in the notch 62, as the tensioning element 42 may still be permitted to move relative to the handle 34 as the handle 34 is being moved proximally.

As mentioned, further proximal movement of the introducer device 20 eventually causes the tensioning element 42 to pull on the anchor 44, after which it slidably ejects from the notch 62 to be removed with the access cannula 18 with the introducer device 20. In other words, the actuation of the tensioning element 42 from the tensioned state to the released state permits the first sloped surface 66 of the anchor 44 and the second sloped surface 68 of the notch 62 to move past one another to facilitate ejection of the anchor 44 from the notch 62. FIG. 6 depicts the implant 22 being decoupled from the introducer device 20. Such function is particularly advantageous owing to the constrains by which the user may manipulate the introducer device 20 while disposed through the access cannula 18. In other words, the shaft 30 of the introducer device 20 is slidably disposed through the access cannula 18, and therefore the user may only withdraw the introducer device 20 in the proximal direction. The anchor 44 and the notch 62 are configured to permit separation with only proximal forces on the anchor 44 from the tensioning element 42. The first and second sloped surfaces 66, 68 effectively transform the axial forces into combined axial-radial forces to move the anchor 44 upwardly within the notch 62 to be ejected.

Figure 7:
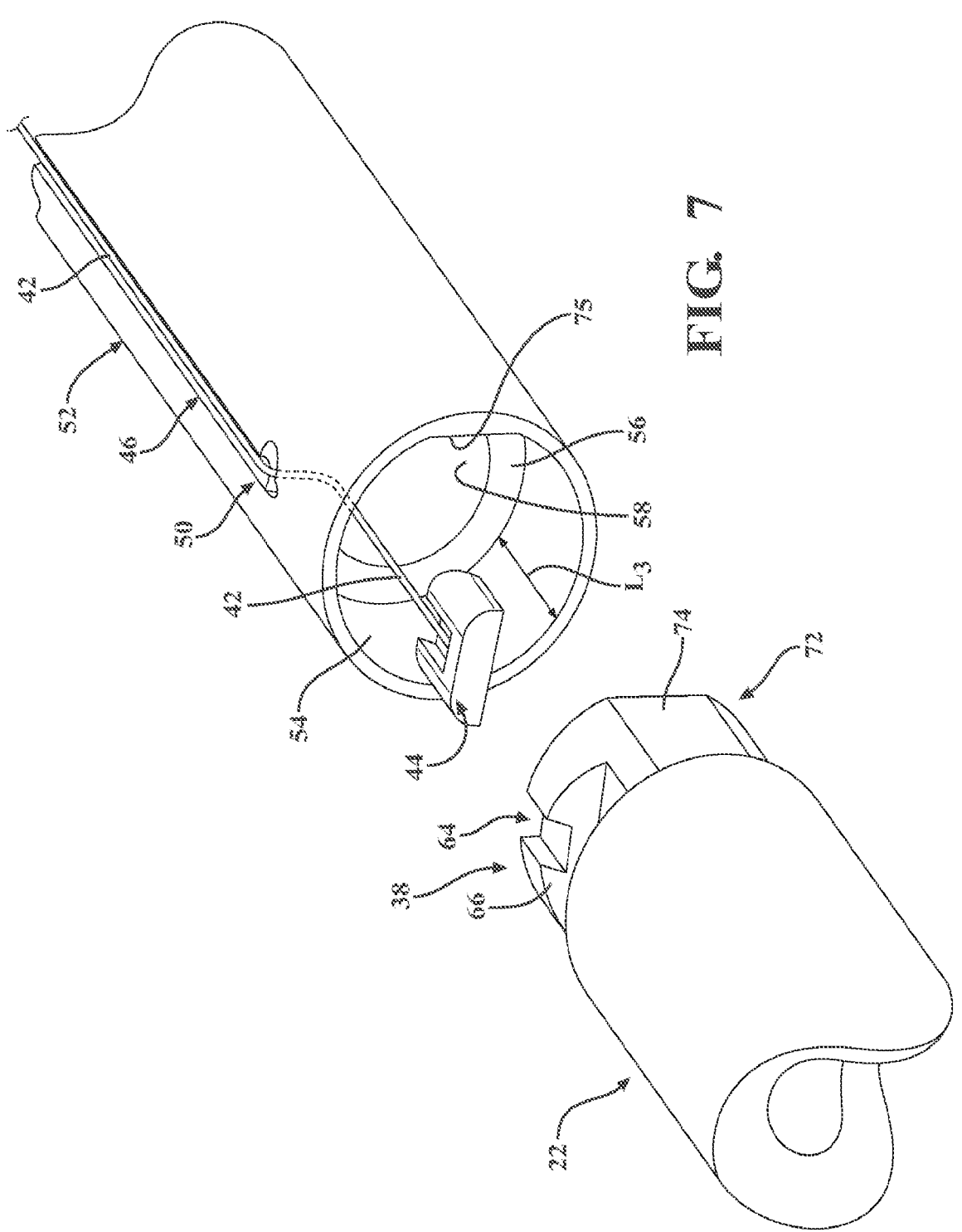
FIG. 7 is another partial perspective view of the system in which the implant is decoupled from the introducer device. An anti-rotation feature is associated with each of the proximal neck and the distal portion.

In certain configurations, the shaft 30 of the introducer device 20 may include geometries configured to further secure the implant 22 to the introducer device 20 in the tensioned state, namely an abutment feature 56 and/or an anti-rotation feature 72. The abutment feature 56 may be a surface from a counterbore that extends from an inner surface 58 of the shaft 30 by a third length L3 (see FIG. 7). The third length L3 may be the same or substantially the same distance as the first length L1 such that the abutment feature 56 abuts a proximal end 70 of the proximal neck 38 of the implant 22. The anti-rotation feature 72 may be positioned radially offset from the notch 62 and include a flat feature 74. A complementary flat feature 75 may be formed within the opening 54 of the shaft 30. With the proximal neck 38 disposed within the distal portion 40, the flat features 74, 75 engage to prevent rotation of the implant 22 relative to the introducer device 20. As shown, the proximal neck 38 of the implant 22 and the opening 54 of the shaft 30 are substantially D-shaped in axial section. It should be appreciated that the proximal neck 38 and the distal portion 40 of the introducer device 20 may include additional geometries to prevent the implant 22 from rotating relative to the introducer device 20.

The proximal neck 38 may define an implant lumen 60 configured to be coaxially arranged with the shaft lumen 48. Further, the handle 34 may be cannulated in order to provide fluid communication between the handle 34, the shaft lumen 48, and the implant lumen 60. The implant lumen 60 is in fluid communication with the retaining element 32, which again includes the apertures to direct the bone cement into the vertebral body adjacent the implant 22. Therefore, once the implant 22 has been deployed, the rod 26 may be decoupled from the retaining element 32 and a portion of the introducer device 20 removed, after which the bone cement may be directed through the shaft lumen 48 and the implant lumen 60. It is noted that integration of the anchor-based mechanism of the present disclosure is achieved without requiring redesign of certain components and workflows of bone cement delivery familiar to users.

Figure 9:
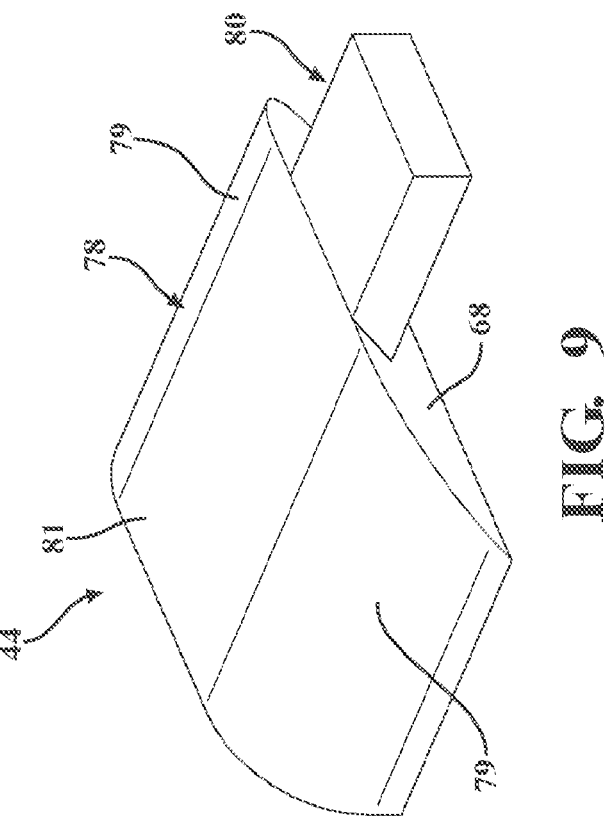
FIG. 9 is a perspective view of another implementation of the anchor.
Figure 8:
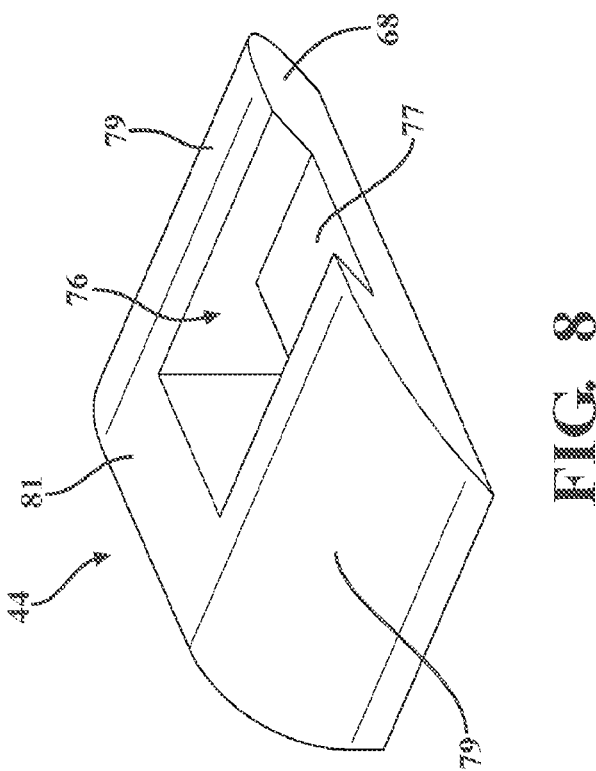
FIG. 8 is a perspective view of an implementation of the anchor.

Referring to FIGS. 8 and 9, exemplary configurations of the anchor 44 are provided. The anchor 44 includes at least two arcuate surfaces 79 contoured to provide the generally semicircular contour of the proximal neck 38 such that, with the anchor 44 disposed within the notch 62, the inner diameter of the distal portion 40 may be snugly and slidably disposed thereover. FIG. 8 shows the anchor 44 defining a recess 76 configured to receive a portion of the tensioning element 42. In other words, the tensioning element 42 may be coupled to the anchor 44 at a position within the recess 76. The tensioning element 42 may be coupled to the anchor 44 in any suitable manner, for example, soldering, laser welding, adhesive, interference fit, or the like. The anchor 44 may further define a slot 77 adjacent to the recess 76 to receive a portion of the tensioning element 42. The slot 77 may extend to the second sloped surface 68. The slot 77 provides for the tensioning element 42 being recessed below an upper surface 81 of the anchor 44 to further facilitate the generally semicircular contour of the proximal neck 38 with the anchor 44 disposed within the notch 62. The implementation of FIG. 9 shows the anchor 44 including a head portion 78 and a tail portion 80 extending from the head portion 78. The head portion 78 includes the second sloped surface 68, and the tail portion 80 may extend from the second sloped surface 68. The tensioning element 42 may be coupled to the tail portion 80.

FIG. 2 shows the actuator 43 being generic in form and disposed on the handle 34. Referring now to FIGS. 10A-11B, more specific exemplary configurations of the actuator 43 are shown in which the actuator 43 maintains tension on the tensioning element 42 in the tensioned state, and releases the tension on the tensioning element 42 upon actuation. As mentioned, the tensioning element 42 is movable relative to the handle 34 in the released state. For example, the tensioning element 42 may be slidable within the handle 34. Therefore, to place the tensioning element 42 in the tensioned state, the user may draw the tensioning element 42 proximally within the handle 34. The user may simultaneously actuate the actuator 43 in order to permit the proximal drawing of the tensioning element 42. The proximal drawing may be achieved by a proximal end of the tensioning element 42 being exposed (i.e., external to the handle), which the user may pinch and pull it taut (see FIGS. 11A and 11B). Once sufficiently pulled to feel resistance from the engagement between the anchor 44 and the notch 62, the user may release the actuator 43 to maintain the tensioning element 34 in the tensioned state. Alternatively, a tensioning actuator (not shown) or other mechanism may be disposed on the handle 34 and configured to proximally draw the tensioning element 42 within the handle 34 until the resistance is achieved.

Figures 10A, 10B, 10C:
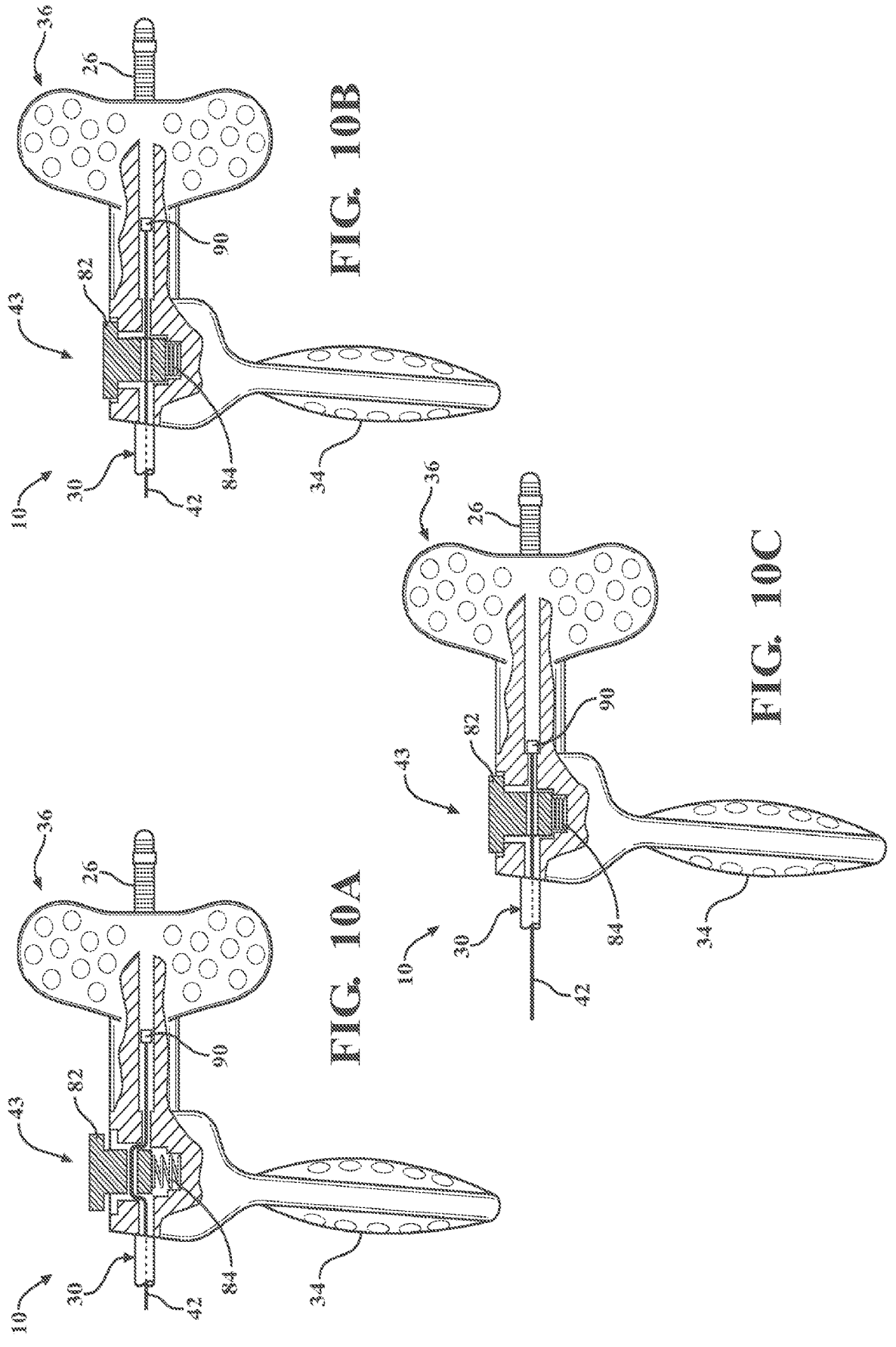
FIG. 10A is a partial sectional view of the introducer device in which the actuator is maintaining tension on the tensioning element.
FIG. 10B is another partial perspective view of the introducer device in which the actuator is actuated to release tension on the tensioning element.
FIG. 10C is another partial perspective view of the introducer device in which a stop member engages a geometry of a handle to prevent further movement of the tensioning element within the handle.
Figure 11B:
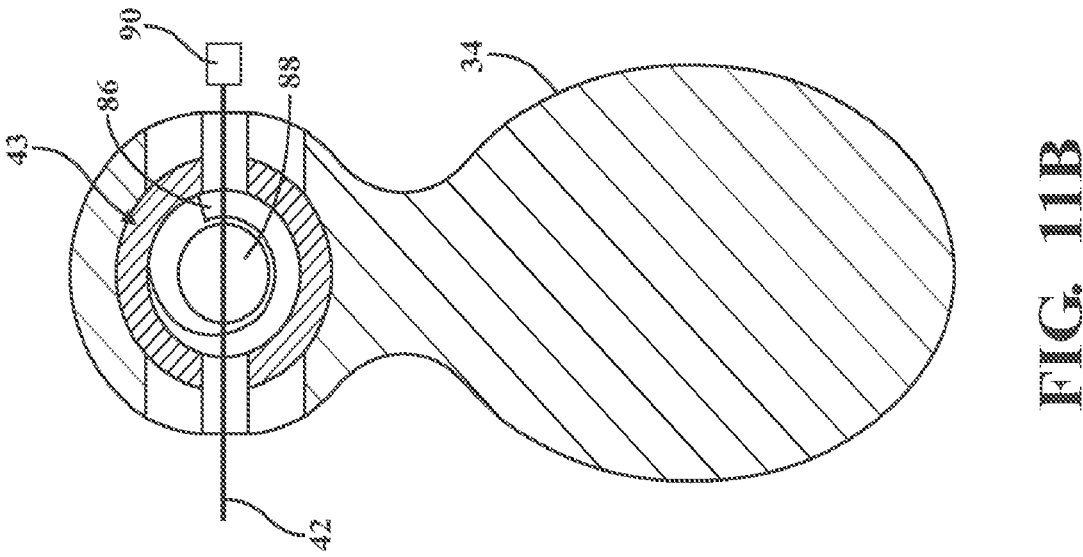
FIG. 11B is another partial perspective view of the introducer device in which the actuator is actuated to release tension on the tensioning element.
Figure 11A:
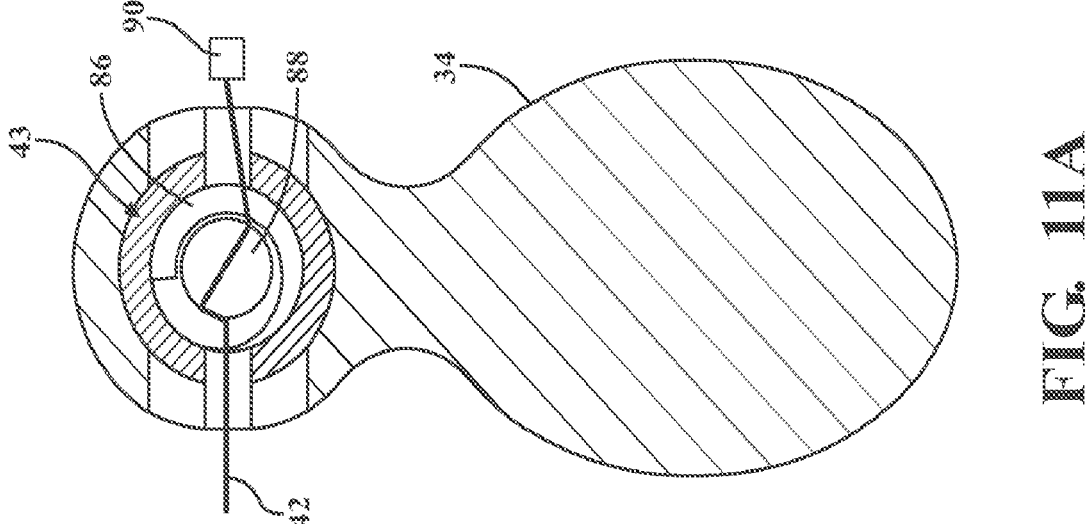
FIG. 11A is a partial sectional view of the introducer device in which the actuator is maintaining tension on the tensioning element.

As shown in FIGS. 10A-10C, the actuator 43 is a pushbutton 82. A biasing member 84 may be coupled to the pushbutton 82, and the actuation of the pushbutton 82 goes against the bias of the biasing member 84. When the pushbutton 82 is not actuated, the pushbutton 82 is biased to maintain in the tensioning element 42 in the tensioned state (or present state if not tensioned). More particularly, the actuator 43 is configured to clamp the tensioning element 42 within the handle 34 to maintain the tensioning element 42 in the tensioned state (see FIG. 10A). The user may effectively grasp the handle 34 and exert a downwards force onto the pushbutton 82 to actuate the pushbutton 82. The actuation of the pushbutton 82 unclamps the tensioning element 42 within the handle 34 to permit the tensioning element 42 to slide relative to the handle 34 (see FIG. 10B). While the pushbutton 82 is illustrated as being positioned on a top side of the introducer device 20, it will be appreciated that the pushbutton 82 may be positioned on any side of and/or at any location relative to the introducer device 20 including any component of the introducer device 20 such as, for example, the handle 34. For instance, the pushbutton 82 may be positioned on a left side of the introducer device 20 such that a user grasping the handle 34 with their right hand may exert a force in a lateral direction onto the pushbutton 82 with their thumb. FIGS. 11A-11B show internal components of the handle 34 with the actuator 43 being a lever. The actuator 43 may include a mandrel 88, and a biasing member 84 coupled to the mandrel 88. The lever is coupled to the mandrel 88 and extends external to the handle 34 (not shown). The biasing member 84 may be a torsion spring. The actuation of the lever 86 against the bias of the biasing member 84 may maintain the tensioning element 42 in the tensioned state (or present state) by twisting or wrapping the tensioning element 42 about the mandrel 88 (see FIG. 11A). The lever 86 may be actuated by twisting, rotating, pulling, bending, and the like. Upon release of the lever 86, the biasing member 84 causes counterposing movement of the lever 86 and the mandrel 88 to permit the tensioning element 42 to be movable within the handle 34 (see FIG. 11B). It should be appreciated that the actuator 43 may be more than one actuator and/or be any type of component that may release tension on the tensioning element such as, but not limited to, a slide switch, a knob, a palm or finger trigger, and the like.

As previously described, the tensioning element 42 may be slidable within the handle 34 by a distance greater than a length of the distal portion 40 within which the proximal neck 38 removably extends. The tensioning element 42 may include a stop member 90 at its proximal end to prevent decoupling of the tensioning element 42 from the handle 34. For example, the stop member 90 may be a block member configured to interfere with internal geometries of the shaft lumen 48 or the handle 34 (see FIG. 10C). In another example, the stop member 90 may be a retention loop. In the released state, the proximal movement of the introducer device 20 causes the tensioning element 42 to pull on the anchor 44, after which it slidably ejects from the notch 62 to be removed with the access cannula 18 with the introducer device 20. The stop member 90 reaching a terminus may provide the proximal force to pull on the anchor 44 (as opposed to the tensioning element 42 continuing to slide within the handle 34). Once the anchor 44 has been separated from the notch 62, the anchor 44 may freely hang or dangle with the tensioning element 42. As the introducer device 20 is removed from the access cannula 18, the anchor 44 is drawn through the access cannula 18. Thereafter, the access cannula 18 remains within the pedicle providing the working channel, and any additional steps of the procedure may be performed therethrough as indicated.

Further inventive aspects of the present disclosure may be made with reference to the following exemplary clauses:

Clause 1—A method for stabilizing a vertebral body with an implant releasably coupled to an introducer device having an actuator, a tensioning element coupled to the actuator, and an anchor coupled to the tensioning element, wherein the implant includes a proximal neck defining a notch, the method including: providing a working channel to within the vertebral body with an access cannula; directing the implant through the access cannula with the tensioning element in a tensioned state in which the anchor is prevented from separating from the notch by a distal portion of the shaft covering the anchor; actuating the actuator to move the tensioning element to a released state in which tension on the element is released; initiating withdrawal of the introducer device from the access cannula with the tensioning element in the released state, wherein the proximal neck of the implant is exposed from the distal portion of the shaft to permit separation of the anchor from the notch and decoupling of the implant from the introducer device; and withdrawing the introducer device from the access cannula.

Clause 2—The method of clause 1, further including, prior to the step of actuating the actuator, delivering bone cement through an implant lumen defined by the proximal neck.

Clause 3—The method of clause 2, further including rotating the introducer device to rotate the implant with an anti-rotation feature disposed on the proximal neck of the implant and within the distal portion of the shaft.

Clause 4—The method of any one of clauses 1-3, further including simultaneously actuating the actuator while tensioning the tensioning element to move the tensioning element to the tensioned state; and releasing the actuator to maintain the tensioning element in the tensioned state.

Clause 5—The method of any one of clauses 1-4, further including actuating an implant actuator to expand the implant; and decoupling a rod of the introducer device from the implant; and removing the rod through the proximal neck of the implant.

Several configurations have been discussed in the foregoing description; however, the configurations discussed herein are not intended to be exhaustive. The terminology which has been used is intended to be in the nature of words of description rather than of limitation, and many modifications and variations are possible in light of the above disclosure. In particular, the functionality of the described configurations may and can be employed in a variety of other surgical and non-surgical applications where it is desirable to prevent unintentional separation of an implant. For example, the system described herein may be used to deploy implants for orthopedic surgery, otolaryngological surgery, and the like.

The invention claimed is:

1. A system for deploying an implant, the system comprising:
an introducer device comprising a handle, an actuator, a shaft extending from the handle, a tensioning element coupled to the actuator and extending along the shaft, and an anchor coupled to the tensioning element; and
an implant comprising a proximal neck configured to be removably disposed within a distal portion of the shaft, the proximal neck defining a notch sized to receive the anchor such that the distal portion of the shaft covers the anchor and prevents separation of the anchor from the notch with the tensioning element in a tensioned state, wherein the actuator is configured to be actuated to release tension on the tensioning element so as to permit removal of the proximal neck from the distal portion of the shaft and separation of the anchor from the notch and decouple the implant from the introducer device.

2. The system of claim 1, wherein the anchor further comprises a first sloped surface, and the proximal neck further comprises a second sloped surface configured to engage the first sloped surface with the tensioning element in the tensioned state.

3. The system of claim 2, wherein the first sloped surface is oriented at an angle relative to a longitudinal axis of the shaft so as to permit the anchor to slidably eject from the notch with proximal movement of the proximal neck relative to the distal portion of the shaft.

4. The system of claim 1, wherein the tensioning element is configured to slide within the handle with the tension released on the tensioning element.

5. The system of claim 4, wherein a distal end of the tensioning element is coupled to the anchor, wherein the tensioning element further comprises a proximal end defining a stop member, and wherein the stop member is configured to engage the actuator to prevent decoupling of the tensioning element from the handle.

6. The system of claim 1, wherein the proximal neck further comprises an antirotation feature positioned radially offset from the notch.

7. The system of claim 6, wherein the proximal neck is substantially D-shaped in an axial section with a flat feature providing the antirotation feature.

8. The system of claim 1, wherein the shaft of the introducer device defines a channel extending longitudinally along the shaft, and wherein the tensioning element is disposed within the channel.

9. The system of claim 8, wherein the channel is defined in an outer surface of the shaft, wherein the shaft is tubular and further defines a shaft lumen, and an aperture extending between the outer surface and the shaft lumen, and wherein the tensioning element passes through the aperture to extend out of the shaft lumen of the distal portion of the shaft.

10. The system of claim 1, wherein the handle is cannulated, wherein the shaft is tubular and defines a shaft lumen, wherein the proximal neck is tubular and defines an implant lumen, wherein the cannulated handle, the shaft lumen, and the implant lumen are coaxially arranged and configured to receive instrumentation for deployment of the implant within a vertebral body.

11. The system of claim 1, wherein the proximal neck of the implant defines a slot, and wherein the tensioning element is removably disposed within the slot with the anchor disposed within the notch.

12. The system of claim 1, wherein the anchor defines a recess configured to receive a portion of the tensioning element.

13. The system of claim 1, wherein the actuator is a pushbutton and further comprises a biasing member coupled to the pushbutton, wherein actuation of the pushbutton against bias of the biasing member is configured to clamp the tensioning element within the handle to maintain the tensioning element in the tensioned state.

14. The system of claim 1, wherein the actuator is a lever and further comprises a mandrel, and a biasing member coupled to the lever, wherein actuation of the lever against bias from the biasing member is configured to twist the tensioning element about the mandrel to maintain the tensioning element in the tensioned state.

15. The system of claim 1, wherein the implant is an intravertebral implant and the system is configured to deploy the intravertebral implant to stabilize a vertebral body.

16. A system for deploying an implant, the system comprising:

an access cannula;

an introducer device comprising a handle, an actuator, a shaft extending from the handle and deployable through the access cannula, a tensioning element coupled to the actuator and extending along the shaft, and an anchor coupled to the tensioning element, wherein the anchor comprises a first sloped surface; and an implant comprising a proximal neck configured to be removably disposed within a distal portion of the shaft, the proximal neck comprising a second sloped surface and defining a notch sized to receive the anchor such that the first sloped surface and the second sloped surface abut one another with the tensioning element in a tensioned state, wherein the actuator is configured to be actuated to release tension on the tensioning element so as to permit the first sloped surface and the second sloped surface to slidably move past one another to facilitate ejection of the anchor from the notch and decouple the implant from the introducer device.

17. The system of claim 16, wherein the anchor further comprises a head portion comprising the first sloped surface, and a tail portion extending from the head portion, and wherein the tensioning element is coupled to the tail portion.

18. A system for deploying an implant, the system comprising:

an introducer device comprising a handle, an actuator, a shaft extending from the handle and comprising a distal portion defining a bore, a tensioning element coupled to the actuator and extending along the shaft, and an anchor coupled to the tensioning element; and an implant comprising a proximal neck removably extending within the distal portion of the shaft, the proximal neck defining a notch engaging the anchor with the tensioning element in a tensioned state, wherein the actuator is configured to be actuated to release tension on the tensioning element in which the tensioning element is slidable within the handle by a distance greater than a length of the distal portion within which the proximal neck removably extends so as to facilitate decoupling the implant from the introducer device.

19. A system for deploying an implant, the system comprising:

an introducer device comprising a handle, an actuator, a shaft extending from the handle, a tensioning element coupled to the actuator and extending along the shaft, and an anchor coupled to the tensioning element; and an implant comprising a proximal neck configured to be removably disposed within a distal portion of the shaft, the proximal neck defining a notch sized to receive the anchor with the tensioning element in a tensioned state, wherein the proximal neck comprises an antirotation feature positioned radially offset from the notch and configured to engage a complementary antirotation feature of the distal portion of the shaft.

20. The system of claim 19, wherein the proximal neck is substantially D-shaped in an axial section with a flat feature providing the antirotation feature.

\* \* \* \* \*